US012419327B2

(12) United States Patent
Deng et al.

(10) Patent No.: US 12,419,327 B2
(45) Date of Patent: Sep. 23, 2025

(54) METHOD FOR PREPARING FEED BY BACTERIA-ENZYME SYNERGISTIC FERMENTATION

(71) Applicant: Jiangnan University, Wuxi (CN)

(72) Inventors: Yu Deng, Wuxi (CN); Yin Mao, Wuxi (CN); Guohui Li, Wuxi (CN)

(73) Assignee: Jiangnan University, Wuxi (CN)

( * ) Notice: Subject to any disclaimer, the term of this patent is extended or adjusted under 35 U.S.C. 154(b) by 857 days.

(21) Appl. No.: 17/680,480

(22) Filed: Feb. 25, 2022

(65) Prior Publication Data

US 2022/0174980 A1 Jun. 9, 2022

Related U.S. Application Data

(63) Continuation of application No. PCT/CN2020/114498, filed on Sep. 10, 2020.

(30) Foreign Application Priority Data

Sep. 30, 2019 (CN) .......................... 201910943375.4
Apr. 10, 2020 (CN) .......................... 202010278169.9

(51) Int. Cl.
*A23K 10/12* (2016.01)
*A23K 10/14* (2016.01)
*C12N 1/20* (2006.01)
*C12N 9/42* (2006.01)
*C12N 9/50* (2006.01)
(Continued)

(52) U.S. Cl.
CPC .............. *A23K 10/12* (2016.05); *A23K 10/14* (2016.05); *C12N 1/205* (2021.05); *C12N 9/2437* (2013.01); *C12N 9/50* (2013.01); *C12P 1/04* (2013.01); *A23V 2400/169* (2023.08); *C12R 2001/25* (2021.05)

(58) Field of Classification Search
CPC ............ A23K 10/12; A23K 10/14; C12P 1/04
See application file for complete search history.

(56) References Cited

FOREIGN PATENT DOCUMENTS

| CN | 105815551 A | 8/2016 |
| CN | 107047928 A | 8/2017 |

(Continued)

OTHER PUBLICATIONS

Machine translation of CN 107259101, published Oct. 20, 2017, pp. 1-14. (Year: 2017).*

(Continued)

*Primary Examiner* — Jenna A Watts
(74) *Attorney, Agent, or Firm* — IPro, PLLC; Na Xu

(57) ABSTRACT

The disclosure discloses a method for preparing feed by bacteria-enzyme synergistic fermentation, belonging to the technical field of fermentation engineering. According to the disclosure, *Lactobacillus plantarum* JUN-DY-6, protease and cellulase are used as a starter, and camellia seed meal or rapeseed meal is used as a substrate. The bacteria-enzyme fermentation product has higher yield of organic acids and flavor substances and better palatability, and can be used for preparing feed additives. The *L. plantarum* of the disclosure can inhibit growth of harmful bacteria such as *Escherichia coli, S. aureus* and *Salmonella* in the intestinal tract of poultry and livestock, and is good for health of the intestinal tract. The method increases the added value of camellia seed meal and rapeseed meal, and is conductive to reuse of waste.

3 Claims, 3 Drawing Sheets

(51) Int. Cl.
*C12P 1/04* (2006.01)
*C12R 1/25* (2006.01)

(56) References Cited

FOREIGN PATENT DOCUMENTS

| | | | |
|---|---|---|---|
| CN | 107259101 | A | 10/2017 |
| CN | 107446852 | A | 12/2017 |
| CN | 109198162 | A | 1/2019 |
| CN | 110583852 | A | 12/2019 |
| CN | 111480729 | A | 8/2020 |
| WO | 02054885 | A1 | 7/2002 |
| WO | 2018206001 | A1 | 11/2018 |

OTHER PUBLICATIONS

Machine translation of CN 107446852, published Dec. 8, 2017, pp. 1-10. (Year: 2017).*
Machine translation of CN 107047928, published Aug. 18, 2017, pp. 1-6. (Year: 2017).*

* cited by examiner

METHOD FOR PREPARING FEED BY BACTERIA-ENZYME SYNERGISTIC FERMENTATION

TECHNICAL FIELD

The disclosure relates to a method for preparing feed by bacteria-enzyme synergistic fermentation, belonging to the technical field of fermentation engineering.

BACKGROUND

Lactic acid bacteria (LAB) are classified into the family Lactobacillaceae. Lactic acid bacteria are Gram-positive, non-spore-forming (except for several genera), non-motile or less-motile, acid-tolerant cocci or bacilli that can produce large amounts of lactic acid using fermentable sugars. Lactic acid bacteria exist widely in human and animal intestines and many foodstuffs. Lactic acid bacteria can not only enhance the nutritive value of food, improve the flavor of food and help improve the preservability of food, but also regulate the normal flora in the human gastrointestinal tract and maintain the micro-ecological balance, and thus are beneficial to human and animal health. By fermenting carbohydrates, Lactic acid bacteria can secrete large amounts of organic acids, lactobacillin, hydrogen peroxide and other bacteriostatic substances to inhibit the growth of spoilage bacteria and thus improve the flavor and quality of food. In recent years, a starter is often artificially added in during soybean meal fermentation to obtain better product flavor and quality, and Lactic acid bacteria are considered as a good starter and can replace additives in food production due to their excellent performance.

*Camellia oleifera*, a multipurpose plant widely distributed in China and western countries, contains a variety of active compounds, has high nutritive peculiarity and medicinal value, and is one of minor oil species that have attracted attention in recent years. The amount of *Camellia* trees planted in China is growing year by year. Traditional methods focus on the oil yield only, not the quality of byproducts, and produce large amounts of *Camellia* seed meal during the production of *Camellia* seed oil. The *Camellia* seed meal has high crude fiber content, low crude protein content, low digestibility (amino acid utilization rate) and extremely high content of toxic substances such as tea saponin. When the *Camellia* seed meal is used as a feed additive, the presence of the tea saponin with hemolytic effect will not only reduce the palatability of the feed, but also cause gastrointestinal poisoning, liver damage, convulsion, coma and even death of animals. At present, feed mills generally use acidulants to achieve the optimum pH for livestock, ignoring the importance of palatability to livestock. In addition, polyphenols such as tannins and flavones in *Camellia* seed meal also cannot be effectively treated at present, resulting in reduced protein digestibility and interference with absorption of some nutrient elements (such as Fe, Ca, etc.). Some large machinery manufacturers have tried to optimize the desolventization of *Camellia* seed meal in the pre-treatment technique to improve the quality of the *Camellia* seed meal, but the processing cost is high and the palatability is poor. Unfermented and detoxified *Camellia* seed meal tastes pungent, bitter and astringent, and has poor palatability and extremely high toxicity for livestock. Therefore, traditionally, *Camellia* seed meal is not used as a feed resource, and it is not well utilized, resulting in vast waste.

Rapeseed meal is a byproduct generated in the production of rapeseed oil, and contains nutritional factors such as crude protein, cellulose, carbohydrates and the like. However, antinutritional factors such as glucosinolates and the like contained in the rapeseed meal limit the feeding value of the rapeseed meal. The presence of the glucosinolates may cause thyroid dysfunction in animals and lead to poisoning of livestock and poultry. In addition, the content of small peptides in the rapeseed meal is low, which is not conducive to the absorption and utilization for livestock. Therefore, effectively reducing the content of glucosinolates in the rapeseed meal and increasing the contents of small peptides and various organic acids are of great significance for increasing the nutritive value of rapeseed meal and solving the problem of supply of raw materials.

With the in-depth research on detoxification methods for rapeseed meal, physical, chemical and biological detoxification methods have been proposed. The physical and chemical detoxification methods have unideal detoxification effects and have safety problems, but the detoxification methods by microbial fermentation are environmentally friendly and have high detoxification rate. The amount of protease produced in microbial fermentation is small, which will result in lower nutrient richness. The enzymolysis can increase the content of peptides in rapeseed meal, but there are some bitter peptides in the product, which affect the taste of the feed and increase the processing cost. In order to reduce the glucosinolates in the rapeseed meal and increases the nutrients, microbial fermentation and enzymolysis can be used in combination. The unique fragrance substances produced by microbial fermentation with Lactic acid bacteria, yeast and *Bacillus subtilis* are used to cover the bitter substances, and the addition of the protease solves the problem of insufficient production of enzymes by microorganisms. Therefore, the combination of microbial fermentation and enzymolysis is of great significance for increasing the feeding value of rapeseed meal.

SUMMARY

A first objective of the disclosure is to provide a method for preparing feed. *Lactobacillus plantarum* JUN-DY-6 and enzymes are used to co-treat a raw material. The raw material contains rapeseed meal or *Camellia* seed meal. The enzymes include protease and cellulase. A moisture content of the raw material is 30-50% (m/m), and a content of the cellulase is 300-400 U/g substrate.

In one implementation, according to the method, the *L. plantarum* JUN-DY-6, the alkaline protease and the cellulase are added to an environment containing *Camellia* seed meal and then fermentation is carried out. A moisture content is 30-50% (m/m), a content of the cellulase is 300-400 U/g substrate, a content of the alkaline protease is 800-1500 U/g substrate, and an inoculum size of the *L. plantarum* JUN-DY-6 is 1-5% (v/m).

The *L. plantarum* JUN-DY-6, disclosed in the patent application CN107446852A, has been collected in China Center for Type Culture Collection on Mar. 23, 2017. The taxonomic name is *Lactobacillus plantarum* JUN-DY-6, the collection number is CCTCC NO: M 2017138, and the collection address is Wuhan University, Wuhan, China.

In one implementation, a cell concentration of the *L. plantarum* JUN-DY-6 is $\geq 10^6$ CFU/g substrate.

In one implementation, a cell concentration of the *L. plantarum* JUN-DY-6 is $\geq 10^5$-$10^7$ CFU/g or $10^5$-$10^7$ CFU/mL.

In one implementation, the fermentation is fermentation at 35° C.-37° C. for 20-30 h.

In one implementation, the moisture content is 50% (m/m), the content of the cellulase is 300 U/g substrate, the content of the alkaline protease is 800 U/g substrate, and the inoculum size of the *L. plantarum* JUN-DY-6 is 5% (v/m).

In one implementation, the moisture content is 40% (m/m), the content of the cellulase is 400 U/g substrate, the content of the alkaline protease is 800 U/g substrate, and the inoculum size of the *L. plantarum* JUN-DY-6 is 4% (v/m).

In one implementation, the moisture content is 30% (m/m), the content of the cellulase is 300 U/g substrate, the content of the alkaline protease is 1200 U/g substrate, and the inoculum size of the *L. plantarum* JUN-DY-6 is 4% (v/m).

In one implementation, according to the method, the *L. plantarum* JUN-DY-6, the cellulase and the neutral protease are added to an environment containing rapeseed meal and then fermentation is carried out. A moisture content in the environment containing rapeseed meal is 30-50% (by mass), an amount of the cellulase used is 300-400 U/g rapeseed meal, and an amount of the neutral protease used is 800-1500 U/g rapeseed meal.

In one implementation of the disclosure, a cell concentration of the *L. plantarum* JUN-DY-6 is $10^5$-$10^8$ CFU/g rapeseed meal.

In one implementation, an amount of the neutral protease used is 1350-1500 U/g rapeseed meal.

In one implementation of the disclosure, the fermentation is fermentation at 35° C.-37° C. for 40-60 h.

In one implementation of the disclosure, a moisture content is 50% (m/m), a content of the cellulase is 300 U/g substrate, a content of the neutral protease is 1500 U/g substrate, and an inoculum size of the *L. plantarum* JUN-DY-6 is 5%.

In one implementation of the disclosure, the moisture content is 40% (m/m), the content of the cellulase is 400 U/g substrate, the content of the neutral protease is 1250 U/g substrate, and the inoculum size of the *L. plantarum* JUN-DY-6 is 4%.

In one implementation of the disclosure, the moisture content is 30% (m/m), the content of the cellulase is 300 U/g substrate, the content of the neutral protease is 1000 U/g substrate, and the inoculum size of the *L. plantarum* JUN-DY-6 is 4%.

A second objective of the disclosure is to provide a starter containing *L. plantarum* JUN-DY-6, protease and cellulase.

In one implementation, the starter is a starter with bacteriostatic effect, including, water, *L. plantarum* JUN-DY-6, alkaline protease and cellulase. A moisture content in the starter is 30-50% (m/m), an enzyme activity unit ratio of the cellulose to the alkaline protease is (3-4):(8-15), and a cell concentration of the *L. plantarum* JUN-DY-6 is $\geq 10^7$ CFU/g or $\geq 10^7$ CFU/mL.

In one implementation, the starter is a starter for preparing fermented rapeseed meal with low glucosinolate content, including *L. plantarum* JUN-DY-6, neutral protease and cellulase. An enzyme activity unit ratio of the cellulase to the neutral protease in the starter is (3-4):(12-15). A cell concentration of the *L. plantarum* JUN-DY-6 is $\geq 10^7$ CFU/g or $\geq 10^7$ CFU/mL.

A third objective of the disclosure is to provide application of the above starter or the above method in food preservation.

In one implementation, the application is to firstly carry out fermentation according to the above method for degrading *Camellia* seed meal and then add the fermentation product to food to inhibit *Staphylococcus aureus*, *Salmonella* and/or *Escherichia coli* from reproducing.

A fourth objective of the disclosure is to provide application of the above starter or the above method in preparation of feed.

In one implementation, the feed uses rapeseed meal or *Camellia* seed meal as a raw material.

In one implementation, the application is used to increase the contents of organic acids.

In one implementation of the disclosure, the application is used to increase the contents of organic acids and reduce the content of glucosinolates in feed.

In one implementation, the organic acids include one or more of lactic acid, citric acid and malic acid.

In one implementation, the application is used to increase aroma substances.

A fifth objective of the disclosure is to provide application of the above starter or the above method in preparation of essences or flavors.

The Disclosure has the Following Beneficial Effects:

(1) The method of bacteria-enzyme synergistic fermentation of rapeseed meal with *L. plantarum* provided by the disclosure greatly increases the bacteriostatic capacity of the rapeseed meal and the contents of organic acids (especially lactic acid), effectively reduces the content of glucosinolates in the rapeseed meal, and improves the palatability, which makes it possible for the rapeseed meal to become a feed additive.

(2) The content of lactic acid in the fermented rapeseed meal prepared by the disclosure is increased by 4.2 times as compared with that before fermentation, and the acid production capacity of the starter is moderate, which will not cause excessive acidification of the rapeseed meal. Compared with the rapeseed meal raw material, the content of glucosinolates in the fermented rapeseed meal is reduced by 38.25%, so the toxicity of the rapeseed meal is greatly reduced.

(3) The method of the disclosure also increases the contents of organic acids and the content of small peptides in the fermented rapeseed meal, increases the added value of the rapeseed meal, and is conductive to reuse of waste.

(4) The method of bacteria-enzyme synergistic fermentation of *Camellia* seed meal with *L. plantarum* provided by the disclosure greatly increases the bacteriostatic capacity of the *Camellia* seed meal and the contents of organic acids (especially lactic acid), effectively reduces the pungent, bitter and astringent tastes of the *Camellia* seed meal, and improves the palatability, which makes it possible for the *Camellia* seed meal to become a feed additive.

(5) The yield of lactic acid in the fermented *Camellia* seed meal prepared by the disclosure is increased by 6.3 times as compared with that before fermentation, and the acid production capacity is moderate, which will not cause excessive acidification of the *Camellia* seed meal.

(6) In the fermentation product obtained by the fermentation method of the disclosure, benzoic acid that can serve as a bacteriostatic agent can be detected, the bacteriostatic rate detected in a 96-well plate is up to 62%, and when used in a feed additive, the fermentation product can improve the immunity of poultry and livestock and establish a good intestinal microbial system. After the bacteria-enzyme synergistic fermentation, different contents of acetyl methyl carbinol, isovaleric acid, 2,3-butanedione, ethyl laurate, nonanoic acid and the like are detected. Many of them are common materials for making essences and flavors, which also greatly improves the palatability of the fermented Camellia seed meal, increases the added value of the Camellia seed meal and is conductive to reuse of waste.

Figure 1:
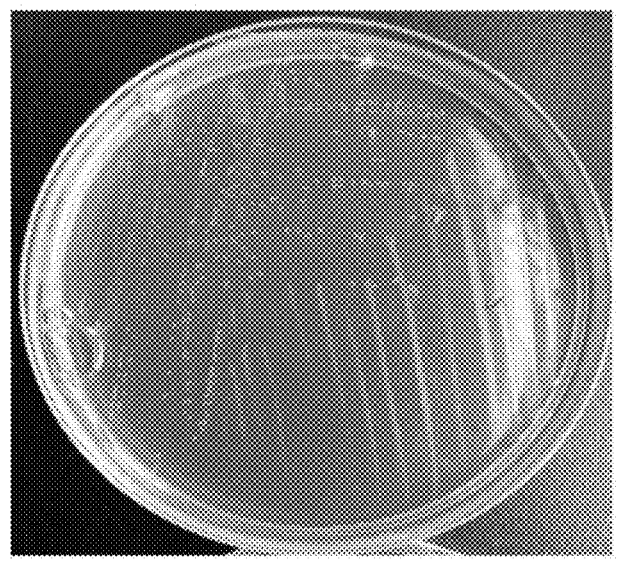
FIG. 1 shows morphology of L. plantarum JUN-DY-6 in a plating medium.

DETAILED DESCRIPTION (I) Method for Determining Diameter of Inhibition Zone of Strain Preparation of indicator bacterial suspension: three indicators, namely E. coli, Salmonella and S. aureus, are inoculated in an LB liquid medium, and cultured at 37° C. for 24 h.

Oxford cup assay: Plates having a diameter of about 90 mm are taken, 15-20 mL of heated and melted nutrient agar is respectively poured into the plates and is made uniformly spread in the plates, and the plates are placed on a horizontal table to solidify the nutrient agar as a bottom layer. An appropriate amount of semisolid nutrient agar medium (with an agar content of 1%) is heated and melted, and cooled to 48-50° C. 0.1-0.2 mL of indicator bacterial suspension is added to every 50-100 mL of the medium. 5 mL of the indicator bacterial suspension is added to each plate, and is made uniformly spread on the bottom layer to serve as a bacterial layer. 4-5 Oxford cups are uniformly placed in each plate at equal intervals for later use. 200 μL of Lactic acid bacteria supernatant is respectively dripped into the Oxford cups in each double-layer plate, and cultured at 37° C. for 10-13 h. Then, the diameter of each inhibition zone is measured to make an evaluation.

(II) Method for Determining Contents of Organic Acids

The contents of organic acids in a fermentation supernatant were determined by an ultraviolet process. The concentration of the organic acid standard is 1 g/L, the temperature of the organic acid column (Aninex Hpx-87H ion exchange column) is 30° C., the mobile phase is a 5 mmol/L $H_2SO_4$ solution, the flow rate is 0.6 mL/min, the injection volume is 20 μL, and the standard and the sample are made to run for 14 min. Spectra are output and analyzed. The peak time and peak area of the sample are compared with those of the standard, and the contents of various organic acids in the sample are calculated.

(III) Method for Determining Contents of Flavor Substances 2 g of fermented meal is accurately weighed and put in a 20 mL headspace bottle. Headspace conditions: The equilibrium temperature is 120° C., the transmission line temperature is 120° C., the sample loop temperature is 120° C., the pressurization time is 0.5 min, the equilibrium time is 30 min, the cycle time is 50 min, the sample loop filling time is 0.5 min, the sample loop equilibrium time is 0.5 min, and the injection time is 1 min.

Example 1: Screening of Strains

Strains were Gram-positive strains with good bacteriostatic effect separated and screened from a Camellia seed meal sample by a plate-dilution separation method. The separation and screening method was as follows:

1. Dilution of mixed strains: The Camellia seed meal sample was weighed, 1 g of the Camellia seed meal was put into an MRS medium and cultured at 37° C. for 24 hours to obtain a bacterial suspension with a cell concentration on the order of magnitude of $1\times10^7$ CFU/mL, and the bacterial suspension was subjected to gradient dilution.

2. Preparation of MRS medium: 10.0 g of peptone, 8.0 g of beef extract, 4.0 g of yeast powder, 20.0 g of glucose, 2.0 g of dipotassium hydrogen phosphate, 2.0 g of triammonium citrate, 5.0 g of sodium acetate, 0.58 g of magnesium sulfate heptahydrate, 0.25 g of manganese sulfate tetrahydrate, 1 mL of Tween 80 and 1 L of distilled water were sterilized at 115° C. for 20 minutes.

Figure 2:
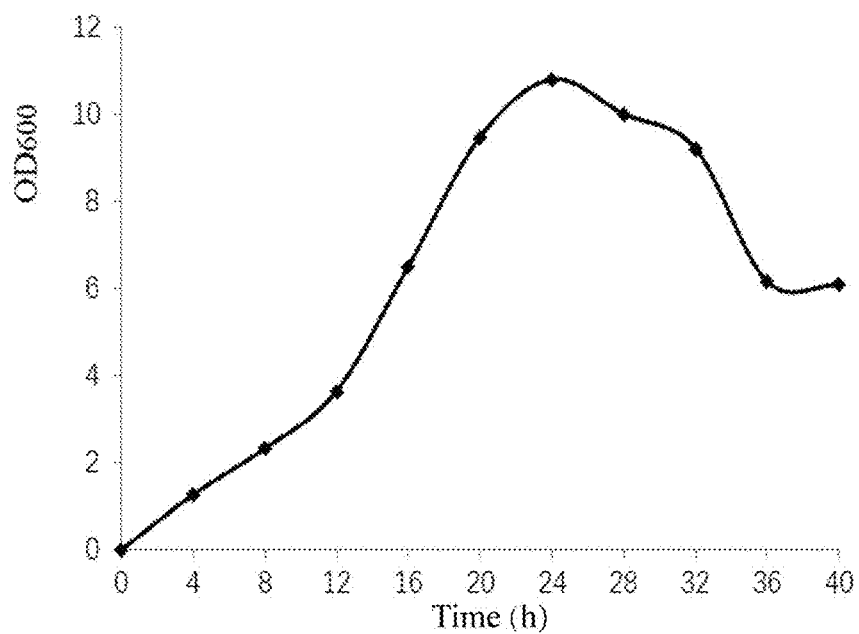
FIG. 2 shows a growth curve of L. plantarum JUN-DY-6 in an MRS medium.

3. Primary screening of strains: 100 μL of bacterial suspension subjected to gradient dilution in step 1 was spread on an MRS solid medium plate with bromocresol purple for primary screening, and cultured at 37° C. for 24 hours. Strains with high growth speed, large colonies and large yellow circle were selected (referring to FIG. 1). After several times of primary screening, 6 Lactic acid bacteria strains were obtained, and numbered DY1-DY6 (referring to FIG. 2 for the growth curve of DY6).

4. Secondary screening of strains: The 6 strains DY1-DY6 obtained by primary screening were inoculated into a liquid medium for secondary screening (10.0 g of peptone, 8.0 g of beef extract, 4.0 g of yeast powder, 20.0 g of glucose, 2.0 g of dipotassium hydrogen phosphate, 2.0 g of triammonium citrate, 5.0 g of sodium acetate, 0.58 g of magnesium sulfate heptahydrate, 0.25 g of manganese sulfate tetrahydrate, 1 mL of Tween 80 and 1 L of distilled water, pH 6.5), and cultured at 37° C. at 200 rpm for 24 h. The bacteriostatic effect of DY1-DY6 was determined.

Figure 3:
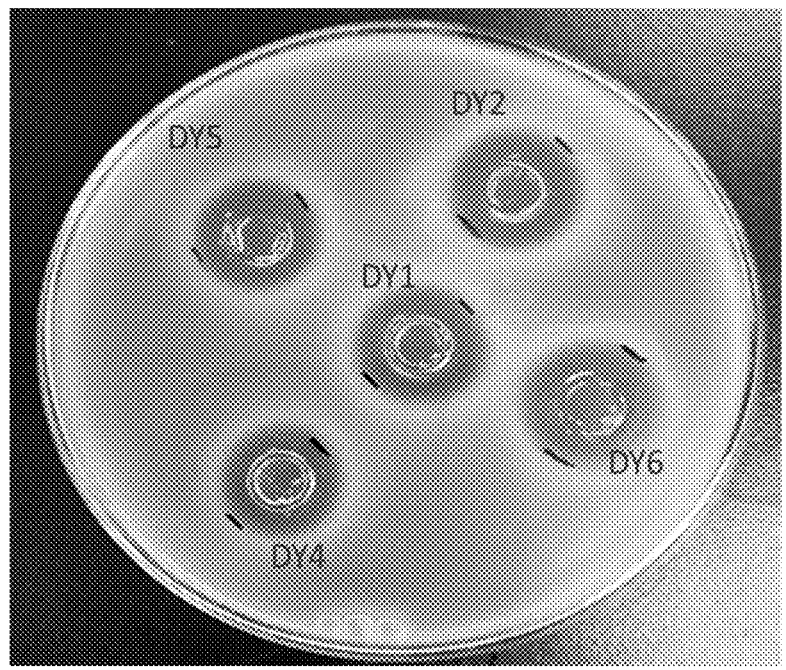
FIG. 3 shows inhibition zones of L. plantarum DY1-DY6 in a zone of inhibition test.

The results showed that DY6 had better inhibitory effect on E. coli, Salmonella and S. aureus than the other 5 strains (referring to Table 1 and FIG. 3). The strain DY6 was finally screened out as the strain for fermenting Camellia seed meal.

TABLE 1

| Bacteriostatic effect of L. plantarum | | | |
|---|---|---|---|
| Strain number | E. coli (mm) | Salmonella (mm) | S. aureus (mm) |
| DY1 | 11.61 | 10.20 | 11.45 |
| DY2 | 12.31 | 12.84 | 13.35 |
| DY3 | 10.46 | 10.75 | 11.40 |
| DY4 | 11.42 | 10.88 | 11.26 |
| DY5 | 11.24 | 10.86 | 12.14 |
| DY6 | 13.27 | 12.38 | 13.67 |

Identification of strain: The obtained strain DY6 was spread on an MRS solid medium, a single colony was picked and amplified using universal primers 1492R and 27F, and the amplification product was delivered to Sangon Biotech (Shanghai) Co., Ltd., and subjected to 16S rRNA sequencing. The sequencing result was compared for homology by Nucleotide BLAST in NCBI. The comparison result showed that the strain has 99% similarity to the 16sRNA of the related type strain (Lactobacillus plantarum WCFS 1, No. 1108) in Genbank, and the strain was determined to be L. plantarum, named Lactobacillus plantarum JUN-DY-6.

The Lactobacillus plantarum JUN-DY-6 has been disclosed in the patent application CN107446852A, and has been collected by China Center for Type Culture Collection on Mar. 23, 2017, and the collection number is CCTCC NO: M 2017138.

Example 2: Fermentation of Camellia Seed Meal with L. plantarum

In order to explore the nutrient composition and fermentation technique having optimal bacteriostatic activity after bacteria-enzyme synergistic fermentation, on the basis of an MRS medium, orthogonal testing was designed to study the effect of the following four components on the fermentation of the Camellia seed meal: water, cellulase, alkaline protease, and L. plantarum JUN-DY-6 bacterial suspension with a cell concentration on the order of magnitude of $1\times10^7$ CFU/mL. The factor levels were shown in Table 2.

TABLE 2

Screening factors and levels of bacteria-enzyme synergistic fermentation components

| Factor | Water (mass fraction %) | Cellulase (U/g) | Alkaline protease (U/g) | JUN-DY-6 (%) |
|---|---|---|---|---|
| Level | 30 | 200 | 800 | 3 |
|  | 40 | 300 | 1200 | 4 |
|  | 50 | 400 | 1500 | 5 |

TABLE 3

Results of orthogonal experiments

| Experiment number | Water | Cellulase (%) | Alkaline protease (U/g) | JUN-DY-6 (%) | Diameter of inhibition zone (mm) |
|---|---|---|---|---|---|
| Experiment 1 | 30 | 200 | 800 | 3 | 14.40 |
| Experiment 2 | 30 | 300 | 1200 | 4 | 16.32 |
| Experiment 3 | 30 | 400 | 1500 | 5 | 15.86 |
| Experiment 4 | 40 | 300 | 1200 | 5 | 16.09 |
| Experiment 5 | 40 | 400 | 1500 | 3 | 15.85 |
| Experiment 6 | 40 | 400 | 800 | 4 | 16.55 |
| Experiment 7 | 50 | 200 | 1500 | 4 | 16.04 |
| Experiment 8 | 50 | 300 | 800 | 5 | 16.62 |
| Experiment 9 | 50 | 400 | 1200 | 3 | 16.19 |

Through the analysis of the orthogonal experiments (referring to Table 3), preferred technological conditions for bacteria-enzyme synergistic fermentation of Camellia seed meal were as follows: the moisture content was 50%, the content of the cellulase was 300 U/g substrate, the content of the alkaline protease was 800 U/g substrate, and the inoculum size of the JUN-DY-6 was 5%.

A 96-well plate method was used to determine the inhibitory effect of a fermentation supernatant of Camellia seed meal on E. coli.

50 μL of E. coli bacterial suspension with a cell concentration of $10^8$ CFU/mL was added to a 96-well plate with 150 μL of filter-sterilized fermentation supernatant (the substrate Camellia seed meal, in which the moisture content was 50% (m/m), the content of cellulase was 300 U/g substrate, the content of alkaline protease was 800 U/g substrate and the inoculum size of JUN-DY-6 was 5% (v/m), was fermented in an MRS fermentation medium at 35° C.-37° C. for 24 h, 2 g of the obtained solid fermentation product was dissolved in 10 mL of sterile water, the mixture was mixed thoroughly and uniformly by vortex for 10 minutes, dispensed in 1.5 mL sterile centrifuge tubes, centrifuged at 12000 rpm for 5 min, and filtered through a sterile filter membrane with a pore size of 0.22 μm on an ultraclean bench to remove solid particles), and cultured at 37° C. for 24 h. Then, the $OD_{600}$ value was determined using a microplate reader. The bacterial suspension inoculated with E. coli and sterile water were used as the control group. Fermented meal (fermented Camellia seed meal) with smaller $OD_{600}$ than control group was screened out.

TABLE 4

96-Well plate test data ($OD_{600}$)

| Technique | Control group | Fermentation group |
|---|---|---|
| Parallel 1 | 0.412 | 0.269 |
| Parallel 2 | 0.384 | 0.258 |
| Parallel 3 | 0.391 | 0.275 |
| Control | 0.17 ± 0.7 |  |
| Background | 0.182 | 0.195 |

Note: To parallels 1, 2 and 3 in the control group, 50 μL of E. coli bacterial suspension and 150 μL of supernatant of Camellia seed meal not subjected to bacteria-enzyme synergistic fermentation were added; to parallels 1, 2 and 3 in the fermentation group, 50 μL of E. coli bacterial suspension and 150 μL of supernatant of bacteria-enzyme synergistic fermentation were added; and the control was 50 μL of E. coli bacterial suspension and 150 μL of sterile water.

The bacteriostasis rate is calculated as follows:

$$\text{Bacteriostasis rate} = \left(1 - \frac{OD_{600} \text{ value of fermentation group} - \text{background}}{OD_{600} \text{ value of control group}}\right) \times 100\%$$

The results (shown in Table 4) showed that the bacteriostasis rate of the control group was −11%, and the bacteriostasis rate of the fermentation group was 62%. The negative bacteriostasis rate in the control group indicated that E. coli continued to grow using unfermented Camellia seed meal as the growth medium.

Example 3: Changes of Contents of Organic Acids Before and After Bacteria-Enzyme Synergistic Fermentation Acidulants can lower the pH of feed, lower the pH in the stomach and increases the activity of digestive enzymes. Acidulants are inferior to organic acids in building healthy intestinal flora of poultry and livestock. For the disease resistance of poultry and livestock, excessive acidulants are often added to feed, which affects the palatability of the feed and increases the cost.

In this example, the fermentation product lactic acid obtained after bacteria-enzyme synergistic fermentation of Camellia seed meal was used instead of the acidulants to well make up for the deficiency of the acidulants in the ability of building healthy intestinal flora.

Figure 4:
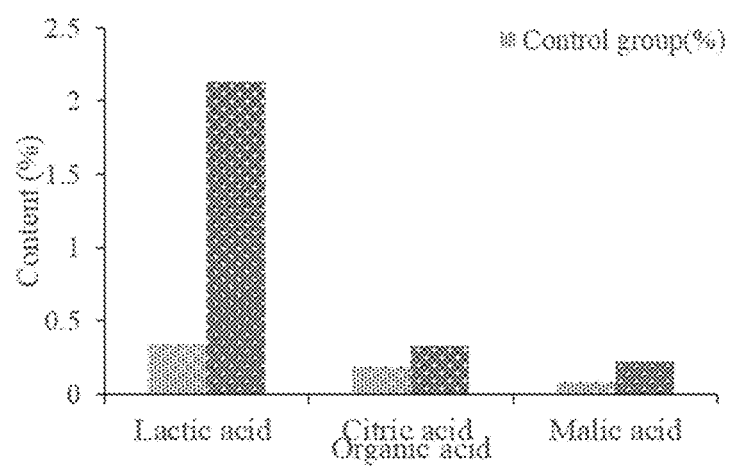
FIG. 4 is a graph showing contents of main organic acids in a fermentation supernatant after bacteria-enzyme synergistic fermentation of Camellia seed meal.

The contents of organic acids in the fermentation supernatant obtained in Example 2 were determined. The results showed that the contents of lactic acid, citric acid and malic acid were significantly increased (referring to Table 5 and FIG. 4). The content of lactic acid was increased by 6.3 times after the fermentation.

TABLE 5

Changes of contents of organic acids before and after fermentation

| Type of organic acid | Content in control group (%) | Content in fermentation group (%) |
|---|---|---|
| Lactic acid | 0.34 | 2.13 |
| Citric acid | 0.19 | 0.33 |
| Malic acid | 0.08 | 0.22 |

Example 4: Aromatic Substances for Improving Palatability of Feed by Fermentation Feed flavors are also known as feed attractants and appetite stimulants, and their action principle is closely related to the taste, smell, respiratory system, digestive system and other functions of animals. The feed flavors can improve the palatability of feed.

Figure 5:
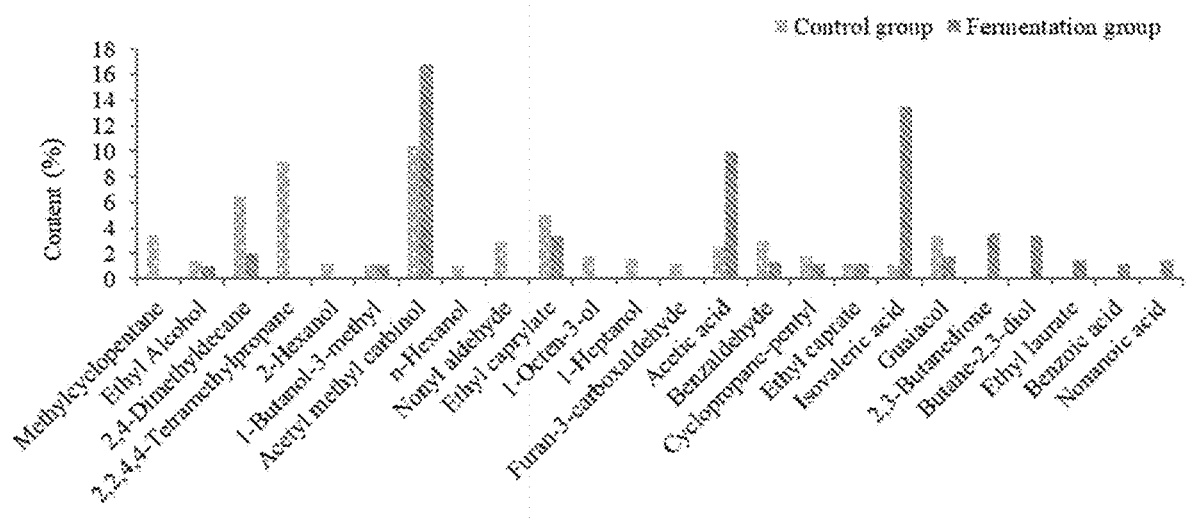
FIG. 5 is a graph showing changes of flavor substances before and after bacteria-enzyme synergistic fermentation of Camellia seed meal.

The contents of flavor substances in the fermentation supernatant obtained in Example 2 were analyzed by gas chromatography. The detection results showed that among the main flavor substances in the fermentation supernatant obtained in Example 2, the contents of acetyl methyl carbinol, ethyl caprylate, 1-octen-3-ol, octanoic acid, ethyl caprate and ethyl laurate are relatively high (referring to Table 6 and FIG. 5). Flavor substances changed significantly after bacteria-enzyme synergistic fermentation with L. plantarum JUN-DY-6, including acetyl methyl carbinol, isovalaric acid, 2,3-butanedione, ethyl laurate, nonanoic acid and the like. Acetyl methyl carbinol, often used as a pharmaceutical intermediate and a food flavoring, is mainly used for preparing cream, milk, yogurt and strawberry type flavors, has a strong creamy, fatty and buttery fragrance, and has a pleasant milk fragrance after being highly diluted. After the fermentation, the content of acetyl methyl carbinol was increased by 61%. Isovalaric acid has a pungent rancid smell, and has a sweet fruity aroma after being highly diluted. The isovalaric acid is often used in baked foods and meat products and mostly used for production of flavors. After the fermentation, the content of isovalaric acid was increased by 13 times. After the bacteria-enzyme synergistic fermentation, different contents of 2,3-butanedione, ethyl laurate and nonanoic acid were detected. These are common materials for making essences and flavors. Benzoic acid can be used as a bacteriostatic agent. In addition, 3% of benzaldehyde was detected in the fermentation product. Although the content was not high, there was a slight pungent odor. After the fermentation, the content of benzaldehyde was reduced to 1.5%. Methylcyclopentane is irritating to eyes, skin, mucosae and upper respiratory tract. After the fermentation, no methylcyclopentane was detected.

TABLE 6

Changes of flavor substances before and after fermentation

| Main flavor substance | Control group (%) | Fermentation group (%) |
|---|---|---|
| Methylcyclopentane | 3.51 | — |
| Ethyl alcohol | 1.4 | 1.01 |
| 2,4-Dimethyldecane | 6.44 | 2.04 |
| 2,2,4,4-Tetramethylpropane | 9.13 | — |
| 2-Hexanol | 1.16 | — |
| 1-Butanol-3-methyl | 1.09 | 1.05 |
| Acetyl methyl carbinol | 10.43 | 16.81 |
| n-Hexanol | 1.01 | — |
| Nonyl aldehyde | 2.92 | — |
| Ethyl caprylate | 5.07 | 3.42 |
| 1-Octen-3-ol | 1.79 | — |
| 1-Heptanol | 1.59 | — |
| Furan-3-carboxaldehyde | 1.2 | — |
| Acetic acid | 2.48 | 9.93 |
| Benzaldehyde | 3 | 1.29 |
| Cyclopropane-pentyl | 1.79 | 1.2 |
| Ethyl caprate | 1.21 | 1.22 |
| Isovaleric acid | 1.04 | 13.46 |
| Dimethoxyphenol | 3.42 | 1.72 |
| 2,3-Butanedione | — | 3.63 |
| Butane-2,3-diol | — | 3.35 |
| Ethyl laurate | — | 1.47 |
| Benzoic acid | — | 1.14 |
| Nonanoic acid | — | 1.51 |

Example 5 Preparation of Starter

Preparation of L. plantarum JUN-DY-6 bacterial suspension: L. plantarum JUN-DY-6 was inoculated in an MRS medium and cultured at 37° C. at 200 r·min$^{-1}$ for 24 h to obtain the L. plantarum bacterial suspension. Optionally, an appropriate amount of protective agent was added to the bacterial suspension, and the mixture was freeze-dried to prepare bacterial powder.

The L. plantarum JUN-DY-6, neutral protease and cellulase were mixed to prepare the starter. An enzyme activity unit ratio of the cellulase to the neutral protease in the starter was (3-4):(12-15). A cell concentration of the L. plantarum JUN-DY-6 was ≥10$^7$ CFU/g or ≥10$^7$ CFU/mL.

The starter also contains auxiliary materials. The auxiliary materials can be conventional auxiliary materials in the art, preferably including one or more of water, lactose, sucrose, maltodextrin, sodium glutamate, gelatin, glycerin, sorbitol, trehalose, yeast extract and β-cyclodextrin.

Example 6 Effect of Different Inoculum Size on Fermented Rapeseed Meal

Water, L. plantarum JUN-DY-6, cellulase and protease were added to rapeseed meal and then fermentation was carried out. The L. plantarum JUN-DY-6 was cultured in an MRS medium at 37° C. for 24 h to obtain a L. plantarum JUN-DY-6 bacterial suspension with a cell concentration on the order of magnitude of 1×10$^8$ CFU/mL. The bacterial suspension was added to the rapeseed meal according to the inoculum size of 1%, 2%, 3%, 4% and 5% (v/m, mL/g substrate). The moisture content in the rapeseed meal raw material for fermentation was adjusted to 50%, the fermentation temperature was controlled at 37° C., the fermentation time was 48 h, the amount of cellulase added was 400 U/g, the protease was neutral protease, and the amount of protease added was 1500 U/g substrate. The detection results of the fermentation products were shown in Table 7.

TABLE 7

Effect of different inoculum size in rapeseed meal on contents of various substance

| Inoculum size (%) | 1 | 2 | 3 | 4 | 5 |
|---|---|---|---|---|---|
| Small peptides (mg · g$^{-1}$) | 85.65 | 87.13 | 86.61 | 86.12 | 85.75 |
| Glucosinolates (μmol · g$^{-1}$) | 22.1 | 18.64 | 15.21 | 16.91 | 15.98 |

TABLE 7-continued

Effect of different inoculum size in rapeseed meal on contents of various substance

| Inoculum size (%) | 1 | 2 | 3 | 4 | 5 |
|---|---|---|---|---|---|
| Total acids (%) | 3.69 | 3.9 | 4.86 | 4.54 | 5.35 |
| Lactic acid (g · L$^{-1}$) | 0.91 | 1.16 | 2.01 | 1.83 | 2.16 |

Example 7 Effect of Different Amount of Neutral Protease Added on Fermented Rapeseed Meal The *L. plantarum* JUN-DY-6 was cultured according to the method in Example 6, the inoculum size was adjusted to 3% (v/m, mL/g), and the bacterial suspension was added to the substrate such that the cell concentration reached 1×10$^6$ CFU/g substrate. Water, the *L. plantarum* JUN-DY-6, cellulase and protease were added to the rapeseed meal and then fermentation was carried out. The rapeseed meal was fermented according to the neutral protease content of 1200, 1350 and 1500 U/g. The moisture content of the entire fermentation raw material was 50%, the fermentation temperature was 37° C., the content of cellulase was 400 U/g substrate, and the fermentation time was 48 h. The rest operations were the same as in Example 6. The detection results of the fermentation products were shown in Table 8.

TABLE 8

Effect of amount of neutral protease added in rapeseed meal on contents of various substances

| Enzyme activity (U/g) | 1200 | 1350 | 1500 |
|---|---|---|---|
| Small peptides (mg · g$^{-1}$) | 80.84 | 86.23 | 86.19 |
| Glucosinolates (μmol · g$^{-1}$) | 15.98 | 15.49 | 15.55 |
| Total acids (%) | 4.85 | 5.27 | 5.04 |
| Lactic acid (g · L$^{-1}$) | 1.95 | 2.09 | 2.11 |

Example 8 Effect of Different Fermentation Time on Fermented Rapeseed Meal

The specific implementation was the same as in Example 6. The *L. plantarum* JUN-DY-6 was cultured according to the method in Example 6. The bacterial suspension was added to the substrate according to the inoculum size of 3% (v/m, mL/g) such that the cell concentration reached 1×10$^6$ CFU/g substrate. The amount of neutral protease added was 1350 U/g. Water, the *L. plantarum* JUN-DY-6, cellulase and the protease were added to rapeseed meal and then fermentation was carried out. The fermentation time was respectively 12 h, 24 h, 36 h, 48 h and 60 h. The moisture content of the entire fermentation raw material was 50%, the fermentation temperature was 37° C., and the amount of cellulase added was 300 U/g substrate. The detection results of the fermentation products were shown in Table 9.

TABLE 9

Effect of different fermentation time of rapeseed meal on contents of various substances

| Time (h) | 12 | 24 | 36 | 48 | 60 |
|---|---|---|---|---|---|
| Small peptides (mg · g$^{-1}$) | 78.91 | 80.57 | 84.5 | 86.35 | 85.88 |

TABLE 9-continued

Effect of different fermentation time of rapeseed meal on contents of various substances

| Time (h) | 12 | 24 | 36 | 48 | 60 |
|---|---|---|---|---|---|
| Glucosinolates (μmol · g$^{-1}$) | 18.32 | 17.41 | 16.34 | 15.48 | 15.1 |
| Total acids (%) | 2.83 | 3.42 | 4.8 | 5.35 | 5.45 |
| Lactic acid (g · L$^{-1}$) | 1.32 | 1.73 | 1.9 | 2.16 | 2.31 |

Example 9 Effect of Different Amount of Cellulase Added on Fermented Rapeseed Meal The specific implementation was the same as in Example 6. The *L. plantarum* JUN-DY-6 was cultured according to the method in Example 6. The bacterial suspension was added to the substrate according to the inoculum size of 3% (v/m, mL/g) such that the cell concentration reached 1×10$^6$ CFU/g substrate. The amount of neutral protease added was adjusted to 1350 U/g, and the fermentation time was 48 h. Water, the *L. plantarum* JUN-DY-6, cellulase and the protease were added to rapeseed meal and then fermentation was carried out. The amount of cellulase was respectively 300, 350 and 400 U/g. The fermentation temperature was 37° C., and the moisture content of the entire fermentation raw material was 50%. The detection results of the fermentation products were shown in Table 10.

TABLE 10

Effect of different amount of cellulase added in rapeseed meal on contents of various substances

| Enzyme activity (U/g) | 300 | 350 | 400 |
|---|---|---|---|
| Small peptides (mg · g$^{-1}$) | 85.9 | 86.01 | 85.93 |
| Glucosinolates (μmol · g$^{-1}$) | 15.44 | 15.18 | 15.29 |
| Total acids (%) | 4.86 | 4.95 | 5.13 |
| Lactic acid (g · L$^{-1}$) | 2.03 | 2.27 | 2.25 |

Example 10 Effect of Different Temperature on Fermented Rapeseed Meal

The specific implementation was the same as in Example 6. The *L. plantarum* JUN-DY-6 was cultured according to the method in Example 6. The bacterial suspension was added to the substrate according to the inoculum size of 3% (v/m, mL/g) such that the cell concentration reached 1×10$^6$ CFU/g substrate. The amount of neutral protease added was 1350 U/g, the fermentation time was 48 h, and the amount of cellulase added was 350 U/g. Water, the *L. plantarum* JUN-DY-6, the cellulase and the protease were added to rapeseed meal and then fermentation was carried out. The fermentation temperature of the rapeseed meal was respectively controlled to 30° C., 35° C., 37° C. and 40° C., and the moisture content of the entire fermentation raw material was 50%. The detection results of the fermentation products were shown in Table 11.

TABLE 11

Effect of different fermentation temperature of rapeseed meal on contents of various substances

| Temperature (° C.) | 30 | 35 | 37 | 40 |
|---|---|---|---|---|
| Small peptides (mg · g$^{-1}$) | 83.21 | 85.05 | 86.65 | 1350 |
| Glucosinolates (μmol · g$^{-1}$) | 17.28 | 16.22 | 15.72 | 350 |
| Total acids (%) | 3.93 | 4.27 | 5.23 | 113.21 |
| Lactic acid (g · L$^{-1}$) | 1.25 | 1.49 | 2.22 | 26.32 |

Example 11 Effect of Different Moisture Content on Fermented Rapeseed Meal

The specific implementation was the same as in Example 6. The *L. plantarum* JUN-DY-6 was cultured according to the method in Example 6. The bacterial suspension was added to the substrate according to the inoculum size of 3% (v/m, mL/g) such that the cell concentration reached 1×10$^6$ CFU/g substrate. The amount of neutral protease added was 1350 U/g, the fermentation time was 48 h, and the amount of cellulase added was 350 U/g, and the fermentation temperature was 37° C. Water, the *L. plantarum* JUN-DY-6, the cellulase and the protease were added to rapeseed meal and then fermentation was carried out. The moisture content in the fermentation raw material was respectively adjusted to 10%, 30%, 50% and 60%. The detection results of the fermentation products were shown in Table 12.

TABLE 12

Effect of different moisture content of rapeseed meal on contents of various substances

| Moisture content (%) | 10 | 30 | 50 | 60 |
|---|---|---|---|---|
| Small peptides (mg · g$^{-1}$) | 82.3 | 85.43 | 86.15 | 93.32 |
| Glucosinolates (μmol · g$^{-1}$) | 16.19 | 15.88 | 15.58 | 16.22 |
| Total acids (%) | 4.72 | 4.84 | 5.12 | 5.03 |
| Lactic acid (g · L$^{-1}$) | 1.84 | 1.95 | 2.06 | 2.19 |

Example 12 Bacteria-Enzyme Synergistic Fermentation of Rapeseed Meal

The *L. plantarum* JUN-DY-6 was cultured according to the method in Example 6. Water, the *L. plantarum* JUN-DY-6, cellulase and protease were added to rapeseed meal and then fermentation was carried out. The moisture content in the rapeseed meal was 50% (m/m), the content of cellulase was 400 U/g substrate, the protease was neutral protease, and the content of protease was 1500 U/g substrate. The bacterial suspension was added to the substrate according to the inoculum size of the *L. plantarum* JUN-DY-6 of 5% (v/m, mL/g) such that the cell concentration reached 1×10$^6$ CFU/g substrate.

The rapeseed meal, into which the protease had been added and the *L. plantarum* had been inoculated, was fermented at 37° C. for 48 h. It was determined that after the completion of the fermentation, the content of small peptides was 85.75 mg/g, the content of glucosinolates was 15.98 μmol·g$^{-1}$, the content of total acids was 5.35%, and the content of lactic acid was 2.16 g·L$^{-1}$ in the rapeseed meal. The content of small peptides was increased by 41.59%, the content of glucosinolates was reduced by 53.27%, the content of total acids was increased by 19.58 times, and the content of lactic acid was increased by 3.24 times.

Example 13 Bacteria-Enzyme Synergistic Fermentation of Rapeseed Meal

The *L. plantarum* JUN-DY-6 was cultured according to the method in Example 6. Water, the *L. plantarum* JUN-DY-6, cellulase and protease were added to rapeseed meal and then fermentation was carried out. The moisture content in the rapeseed meal was 50% (m/m), the content of cellulase was 300 U/g substrate, the protease was neutral protease, and the content of protease was 1350 U/g substrate. The bacterial suspension was added to the substrate according to the inoculum size of the *L. plantarum* JUN-DY-6 of 3% (v/m, mL/g) such that the cell concentration reached 1×10$^6$ CFU/g substrate.

The rapeseed meal, into which the protease had been added and the *L. plantarum* had been inoculated, was fermented at 37° C. for 60 h. It was determined that after the completion of the fermentation, the content of small peptides was 85.88 mg/g, the content of glucosinolates was 15.10 μmol·g$^{-1}$, the content of total acids was 5.45%, and the content of lactic acid was 2.31 g·L$^{-1}$ in the rapeseed meal. The content of small peptides was increased by 41.80%, the content of glucosinolates was reduced by 55.84%, the content of total acids was increased by 19.96 times, and the content of lactic acid was increased by 3.53 times.

Example 14 Bacteria-Enzyme Synergistic Fermentation of Rapeseed Meal

Water, the *L. plantarum* JUN-DY-6, cellulase and protease were added to the rapeseed meal and then fermentation was carried out. The moisture content was 50% (m/m), the content of cellulase was 350 U/g substrate, the protease was neutral protease, and the content of protease was 1350 U/g substrate. The *L. plantarum* JUN-DY-6 was cultured according to the method in Example 2, and the bacterial suspension was added to the substrate according to the inoculum size of 3% (v/m, mL/g) such that the cell concentration reached 1×10$^6$ CFU/g substrate.

The rapeseed meal, into which the protease had been added and the *L. plantarum* had been inoculated, was fermented at 40° C. for 48 h. It was determined that after the completion of the fermentation, the content of small peptides was 113.21 mg/g, the content of glucosinolates was 26.32 μmol·g$^{-1}$, the content of total acids was 2.29%, and the content of lactic acid was 1.12 g·L$^{-1}$ in the rapeseed meal. The content of small peptides was increased by 86.94%, the content of glucosinolates was reduced by 23.04%, the content of total acids was increased by 10.26 times, and the content of lactic acid was increased by 1.20 times.

Example 15 Bacteria-Enzyme Synergistic Fermentation of Rapeseed Meal (1) Water, *L. plantarum* JUN-DY-6, cellulase and protease were added to the rapeseed meal and then fermentation was carried out. The moisture content in the rapeseed meal was 50% (m/m), the content of cellulase was 400 U/g substrate, the protease was neutral protease, and the content of protease was 1500 U/g substrate. The *L. plantarum* JUN-DY-6 was cultured according to the method in Example 2, and the bacterial suspension was added to the substrate according to the inoculum size of 4% (v/m, mL/g) such that the cell concentration reached 1×10$^6$ CFU/g substrate.

The rapeseed meal, into which the protease had been added and the *L. plantarum* had been inoculated, was fermented at 37° C. for 48 h. It was determined that after the completion of the fermentation, the content of small peptides was 86.12 mg/g, the content of glucosinolates was 16.91 μmol·g$^{-1}$, the content of total acids was 4.54%, and the content of lactic acid was 1.83 g·L$^{-1}$ in the rapeseed meal. The content of small peptides was increased by 42.17%, the content of glucosinolates was reduced by 50.56%, the content of total acids was increased by 16.46 times, and the content of lactic acid was increased by 2.59 times.

Example 16 Bacteria-Enzyme Synergistic Fermentation of Rapeseed Meal (1) Water, *L. plantarum* JUN-DY-6, cellulase and protease were added to the rapeseed meal and then fermentation was carried out. The moisture content in the rapeseed meal was 30% (m/m), the content of cellulase was 350 U/g substrate, the protease was neutral protease, and the content of protease was 1500 U/g substrate. The *L. plantarum* JUN-DY-6 was cultured according to the method in Example 2, and the bacterial suspension was added to the substrate according to the inoculum size of 3% (v/m, mL/g) such that the cell concentration reached 1×10$^6$ CFU/g substrate.

The rapeseed meal, into which the protease had been added and the *L. plantarum* had been inoculated, was fermented at 37° C. for 48 h. It was determined that after the completion of the fermentation, the content of small peptides was 85.07 mg/g, the content of glucosinolates was 17.12 μmol·g$^{-1}$, the content of total acids was 4.79%, and the content of lactic acid was 1.69 g·L$^{-1}$ in the rapeseed meal. The content of small peptides was increased by 40.47%, the content of glucosinolates was reduced by 49.94%, the content of total acids was increased by 17.42 times, and the content of lactic acid was increased by 2.31 times.

Example 17 Bacteria-Enzyme Synergistic Fermentation of Rapeseed Meal (1) Water, *L. plantarum* JUN-DY-6, cellulase and protease were added to the rapeseed meal and then fermentation was carried out. The moisture content in the rapeseed meal was 60% (m/m), the content of cellulase was 300 U/g substrate, the protease was neutral protease, and the content of protease was 1350 U/g substrate. The *L. plantarum* JUN-DY-6 was cultured according to the method in Example 2, and the bacterial suspension was added to the substrate according to the inoculum size of 3% (v/m, mL/g) such that the cell concentration reached 1×10$^6$ CFU/g substrate.

The rapeseed meal, into which the protease had been added and the *L. plantarum* had been inoculated, was fermented at 30° C. for 36 h. It was determined that after the completion of the fermentation, the content of small peptides was 80.82 mg/g, the content of glucosinolates was 17.34 μmol·g$^{-1}$, the content of total acids was 2.89%, and the content of lactic acid was 1.01 g·L$^{-1}$ in the rapeseed meal. The content of small peptides was increased by 33.45%, the content of glucosinolates was reduced by 49.3%, the content of total acids was increased by 10.12 times, and the content of lactic acid was increased by 0.98 time.

Example 18 Comparison of Components in Fermented Rapeseed Meal Prepared Under Different Conditions (1) Changes of Contents of Total Acids and Organic Acids Before and After Fermentation Acidulants can lower the pH of feed, lower the pH in the stomach and increases the activity of digestive enzymes. Acidulants are inferior to organic acids in building healthy intestinal flora of poultry and livestock. For the disease resistance of poultry and livestock, excessive acidulants are often added to feed, which affects the palatability of the feed and increases the cost.

In this example, the fermentation product lactic acid obtained after bacteria-enzyme synergistic fermentation of rapeseed meal was used instead of the acidulants to well make up for the deficiency of the acidulants in the ability of building healthy intestinal flora. The contents of total acids and organic acids in the fermentation products obtained in different examples were determined. It was found that the contents of total acids and organic acids were significantly increased (referring to Table 13). The content of total acids could be increased by up to 19.96 times, and the content of lactic acid could be increased by up to 3.5 times.

(2) Changes of Content of Glucosinolates Before and After Bacteria-Enzyme Synergistic Fermentation Glucosinolates are the main antinutritional factors in rapeseed meal that limit the feedability of rapeseed meal. Microbial fermentation can reduce the content of glucosinolates in the rapeseed meal and lower the toxicity of the rapeseed meal. After determining the content of glucosinolates in the fermented rapeseed meal supernatant in different examples, it can be seen that after the bacteria-enzyme synergistic fermentation, the content of glucosinolates in the rapeseed meal was significantly reduced (Table 13) by up to 55.84%.

(3) Changes of Content of Small Peptides Before and After Bacteria-Enzyme Synergistic Fermentation The increase in the content of small peptides is mainly due to the enzymolysis of macromolecular proteins in the rapeseed meal by the protease. Through the comparison of degradation effects of different proteases, it was determined that the content of small peptides in the fermented rapeseed meal in different examples could be increased by up to 86.94%.

TABLE 13

Changes of contents of various substances in rapeseed meal before and after fermentation

| Type | Rapeseed meal raw material | Example 12 | Example 13 | Example 14 | Example 15 | Example 16 | Example 18 |
|---|---|---|---|---|---|---|---|
| Small peptides (mg · g$^{-1}$) | 60.56 | 85.75 | 85.88 | 113.21 | 86.12 | 85.07 | 80.82 |
| Total acids (%) | 0.26 | 5.35 | 5.45 | 2.93 | 4.54 | 4.79 | 2.89 |
| Lactic acid (g · L$^{-1}$) | 0.51 | 2.16 | 2.31 | 1.12 | 1.83 | 1.69 | 1.01 |
| Citric acid (g · L$^{-1}$) | 0.10 | 0.45 | 0.44 | 0.18 | 0.45 | 0.21 | 0.22 |
| Malic acid (g · L$^{-1}$) | 0.12 | 0.18 | 0.25 | 0.15 | 0.24 | 0.18 | 0.17 |
| Glucosinolates (μol · g$^{-1}$) | 34.20 | 15.98 | 15.10 | 26.32 | 16.91 | 17.12 | 17.34 |

Comparative Example 1 Preparation of Fermented Rapeseed Meal with Different *L. plantarum* Strains The *L. plantarum* JUN-DY-6 was replaced with other *L. plantarum* strains preserved in the laboratory, and fermentation was carried out according to the same method as in Example 12. The contents of various substances in the fermented feed were detected. The results were shown in Table 14.

| Strain | Glucosinolates (μmol/g) | Small peptides (mg/g) | Total acids (%) |
|---|---|---|---|
| DY1 | 20.25 | 84.31 | 4.00 |
| DY2 | 30.93 | 84.10 | 3.63 |
| DY3 | 26.03 | 84.85 | 2.12 |
| DY4 | 33.14 | 82.81 | 1.82 |
| DY5 | 25.79 | 86.44 | 2.24 |

Although the disclosure has been disclosed as above in the preferred examples, it is not intended to limit the disclosure. Any person familiar with the art can make various changes and modifications without departing from the spirit and scope of the disclosure. Therefore, the protection scope of the disclosure should be as defined in the claims.

What is claimed is:

1. A method for preparing a feed composition, comprising:
providing a raw material comprising: (a) camellia seed meal, and (b) enzymes, wherein the enzymes comprise alkaline protease and cellulase, to produce a mixture,
adding to the mixture an inoculum of *Lactobacillus plantarum* (*L. plantarum*) JUN-DY-6 collection number CCTCC M 2017138, at 1 to 5% to produce a fermentation mixture; and
fermenting the fermentation mixture to produce a feed composition,
wherein a moisture content of the raw material is 30 to 50%;
wherein the cellulase is present in the mixture at 300 to 400 U/g substrate;
wherein the alkaline protease is present in the mixture at 800 to 1200 U/g substrate; and
wherein the *L. plantarum* JUN-DY-6 is present at a concentration of greater than or equal to $10^6$ CFU/g substrate.

2. The method according to claim 1, wherein the fermenting is conducted at 35° C. to 37° C. for at least 20 hours.

3. The method according to claim 1, wherein the fermenting is conducted for 40 to 60 hours.

* * * * *